(12) United States Patent
Watts et al.

(10) Patent No.: US 8,889,176 B2
(45) Date of Patent: *Nov. 18, 2014

(54) METHOD OF MANAGING OR TREATING PAIN

(75) Inventors: Peter James Watts, Nottingham (GB); Jonathan David Castile, Nottingham (GB); William Columbus Lafferty, Leicester (GB); Alan Smith, Nottingham (GB)

(73) Assignee: Depomed, Inc., Newark, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/541,314

(22) Filed: Jul. 3, 2012

(65) Prior Publication Data

US 2012/0277267 A1 Nov. 1, 2012

Related U.S. Application Data

(60) Continuation of application No. 12/047,388, filed on Mar. 13, 2008, now Pat. No. 8,216,604, which is a division of application No. 10/753,628, filed on Jan. 8, 2004, now abandoned.

(30) Foreign Application Priority Data

Jan. 10, 2003 (GB) .................................. 0300531.1

(51) Int. Cl.
| | | |
|---|---|---|
| A61F 13/00 | (2006.01) | |
| A61K 31/445 | (2006.01) | |
| A01N 43/40 | (2006.01) | |
| A01N 43/16 | (2006.01) | |
| A61K 31/35 | (2006.01) | |

(52) U.S. Cl.
USPC ............................ 424/434; 514/317; 514/453

(58) Field of Classification Search
USPC ........................................................ 424/434
See application file for complete search history.

(56) References Cited

U.S. PATENT DOCUMENTS

| | | |
|---|---|---|
| 2,125,212 A | 7/1938 | Wright |
| 2,730,483 A | 1/1956 | Buckwalter |
| 3,164,600 A | 1/1965 | Janssen et al. |
| 4,464,378 A | 8/1984 | Hussain |
| 4,486,423 A | 12/1984 | Kenyhercz |
| 4,609,640 A | 9/1986 | Morishita et al. |
| 4,613,500 A | 9/1986 | Suzuki et al. |
| 4,659,696 A | 4/1987 | Hirai et al. |
| 4,681,887 A | 7/1987 | Megyeri et al. |
| 4,806,341 A | 2/1989 | Chien et al. |
| 4,826,683 A | 5/1989 | Bates |
| 4,861,760 A | 8/1989 | Mazuel et al. |
| 4,915,948 A | 4/1990 | Gallopo et al. |
| 4,981,875 A | 1/1991 | Leusner et al. |
| 4,983,385 A | 1/1991 | Hasegawa et al. |
| 5,147,648 A | 9/1992 | Bannert |
| 5,200,180 A | 4/1993 | Bannert |
| 5,236,714 A | 8/1993 | Lee et al. |
| 5,238,917 A | 8/1993 | Fujii et al. |
| 5,318,780 A | 6/1994 | Viegas et al. |
| 5,346,703 A | 9/1994 | Viegas et al. |
| 5,397,771 A | 3/1995 | Bechgaard et al. |
| 5,456,745 A | 10/1995 | Roreger et al. |
| 5,457,093 A | 10/1995 | Cini et al. |
| 5,508,042 A | 4/1996 | Oshlack et al. |
| 5,543,434 A | 8/1996 | Weg |
| 5,655,517 A | 8/1997 | Coffee |
| 5,707,644 A | 1/1998 | Illum |
| 5,735,263 A | 4/1998 | Rubsamen et al. |
| 5,756,483 A | 5/1998 | Merkus |
| 5,855,517 A | 1/1999 | Lepold |
| 5,910,301 A | 6/1999 | Farr et al. |
| 5,955,502 A | 9/1999 | Hansen et al. |
| 6,090,368 A | 7/2000 | Zia et al. |
| 6,387,917 B1 | 5/2002 | Illum et al. |
| 6,432,440 B1 | 8/2002 | Watts et al. |
| 6,541,021 B1 | 4/2003 | Johnson et al. |
| 6,610,271 B2 | 8/2003 | Wermeling |
| 6,663,883 B1 | 12/2003 | Akiyama et al. |
| 6,667,279 B1 | 12/2003 | Hessert et al. |

(Continued)

FOREIGN PATENT DOCUMENTS

| | | |
|---|---|---|
| AU | 7558091 B2 | 3/1994 |
| AU | 6156596 A | 12/1996 |

(Continued)

OTHER PUBLICATIONS

Office Action issued Oct. 17, 2012 in EP Application No. 04 701 381.8.

(Continued)

*Primary Examiner* — Layla Soroush

(74) *Attorney, Agent, or Firm* — McDermott Will & Emery LLP

(57) ABSTRACT

A composition for the intranasal delivery of fentanyl or a pharmaceutically acceptable salt thereof to an animal includes an aqueous solution of fentanyl or a pharmaceutically acceptable salt thereof and a pharmaceutically acceptable additive selected from (i) a pectin and (ii) a poloxamer and chitosan or a salt or derivative thereof; provided that when the composition comprises a pectin it is substantially free of divalent metal ions; and which, in comparison to a simple aqueous solution of fentanyl administered intranasally at the same dose, provides a peak plasma concentration of fentanyl ($C_{max}$) that is from 10 to 80% of that achieved using a simple aqueous solution of fentanyl administered intranasally at an identical fentanyl dose. A method for treating or managing pain by intranasally administering the composition is also disclosed.

40 Claims, 2 Drawing Sheets

(56) References Cited

U.S. PATENT DOCUMENTS

| | | | |
|---|---|---|---|
| 6,777,000 | B2 | 8/2004 | Ni et al. |
| 8,216,604 | B2 | 7/2012 | Watts et al. |
| 2002/0197324 | A1 | 12/2002 | Watts et al. |
| 2003/0077300 | A1 | 4/2003 | Wermeling |
| 2004/0166067 | A1 | 8/2004 | Watts et al. |
| 2005/0142072 | A1 | 6/2005 | Birch et al. |
| 2007/0092535 | A1 | 4/2007 | Watts et al. |
| 2007/0110677 | A1 | 5/2007 | Watts et al. |
| 2007/0231269 | A1 | 10/2007 | Birch et al. |
| 2011/0105551 | A1 | 5/2011 | Birch et al. |
| 2011/0182857 | A1 | 7/2011 | Watts et al. |

FOREIGN PATENT DOCUMENTS

| | | |
|---|---|---|
| AU | 6257896 A | 12/1996 |
| AU | 199659244 B2 | 12/1998 |
| AU | 199964928 B2 | 8/2003 |
| AU | 200037561 B2 | 1/2004 |
| DE | 19627392 A1 | 1/1997 |
| EP | 0227494 A1 | 7/1987 |
| EP | 0255485 A2 | 2/1988 |
| EP | 0267617 A1 | 5/1988 |
| EP | 0289512 A1 | 11/1988 |
| EP | 0306454 A2 | 3/1989 |
| EP | 0491076 | 6/1992 |
| EP | 0518798 A2 | 12/1992 |
| EP | 0571671 A1 | 12/1993 |
| EP | 0460020 B1 | 4/1994 |
| EP | 0651993 A1 | 5/1995 |
| EP | 0757910 A1 | 2/1997 |
| EP | 1108423 A1 | 6/2001 |
| EP | 1642578 A2 | 4/2006 |
| GB | 2378383 A | 2/2003 |
| JP | 62181228 A | 8/1987 |
| JP | 62236862 A | 10/1987 |
| JP | 63502186 T | 8/1988 |
| JP | 07-503481 A | 4/1995 |
| JP | 08-508472 A | 9/1996 |
| JP | 8510467 T | 11/1996 |
| JP | 8510731 T | 11/1996 |
| JP | 10506376 T | 6/1998 |
| JP | 2000-229859 A | 8/2000 |
| JP | 2001-002589 A | 1/2001 |
| JP | 2001089359 A | 4/2001 |
| JP | 2001524094 T | 11/2001 |
| WO | 8203768 A1 | 11/1982 |
| WO | 8704350 A1 | 7/1987 |
| WO | 8810121 A1 | 12/1988 |
| WO | 9007333 A1 | 7/1990 |
| WO | 9009780 A1 | 9/1990 |
| WO | 9103271 A1 | 3/1991 |
| WO | 9106282 A1 | 5/1991 |
| WO | 9315737 A1 | 8/1993 |
| WO | 9410987 A1 | 5/1994 |
| WO | 9422445 A2 | 10/1994 |
| WO | 9427576 A1 | 12/1994 |
| WO | 9427578 A1 | 12/1994 |
| WO | 9502416 A1 | 1/1995 |
| WO | 9522315 A1 | 8/1995 |
| WO | 9603142 A1 | 2/1996 |
| WO | 9633694 A1 | 10/1996 |
| WO | 9704780 A2 | 2/1997 |
| WO | 9802187 A1 | 1/1998 |
| WO | 9834596 A2 | 8/1998 |
| WO | 9847535 A1 | 10/1998 |
| WO | 9909962 A1 | 3/1999 |
| WO | 9913799 A1 | 3/1999 |
| WO | 9927905 A1 | 6/1999 |
| WO | 9945963 A1 | 9/1999 |
| WO | 0012063 A1 | 3/2000 |
| WO | 0016750 A1 | 3/2000 |
| WO | 0016751 A1 | 3/2000 |
| WO | 0024373 A1 | 5/2000 |
| WO | 0047203 A1 | 8/2000 |
| WO | 0129046 A2 | 4/2001 |
| WO | 0135942 A2 | 5/2001 |
| WO | 0158447 A1 | 8/2001 |
| WO | 0168140 A2 | 9/2001 |
| WO | 0197780 A2 | 12/2001 |
| WO | 0200195 A2 | 1/2002 |
| WO | 0209707 A1 | 2/2002 |
| WO | 02051380 A1 | 7/2002 |
| WO | 02067897 A2 | 9/2002 |
| WO | 03080021 A2 | 10/2003 |
| WO | 03080022 A2 | 10/2003 |

OTHER PUBLICATIONS

"Fentanyl 25-pg/0.1-mL Nasal Spray," International Journal of Pharmaceutical Compounding,, 4('1)57 (Jan./Feb. 2000).

ABPI Compendium of Data Sheets and Summaries of Product Characteristics 1996-97, Datapharm Publications Limited, London, pp. 472-473 (1996-97).

Ahmedzai S., et al., "Nebulised drugs in palliative care," Thorax 52 (Suppl. 2)(S75-S77 (1997).

Aspden, et al. "Chitosan as a nasal delivery system: the effect of chitosan solutions on in Vitro and in Vivo mucociliary transport rates in human turbinates and volunteers", J. Pharm. Sci. 86(4):509-13 (1997).

Axelos & Thibault, "The Chemistry of Low-Methoxyl Pectin Gelatin" in The Chemistry and technology of Pectin, pp. 109-118, Academic Press: New York (1991).

Aydin & Akbuga, "Preparation and evaluation of pectin beads", Int. J. Pharm., 137:133-36 (1996).

B.A., Zhubanov et al., "Application of carboxyl methyl cellulose and pectic acid to prolong clophelin action", Izvestiya Natsional'noi Akademii Nauk Respubliki Kazakhstan, Seriya Khimecheskaya, (1), pp. 61-65 (1993).

B.I. Nurmukhambetova et al. "Interaction of cephedrin with polyelectrolytes", News of the National Academy of Sciences of Republic of Kazakhstan, Chemical Series, vol. 3, pp. 58-61 (1995).

Borland, M.D., et al., "Intranasal fentanyl reduces acute pain in children in the ermergency department: A safety and efficacy study," Emergency Medicine 14:275-280 (2002).

British Search Report Issued Jan. 27, 2004 in GB Application No. GB0300531.1 (cited in U.S. Appl. No. 10/753,628.

Brown, et al. "Spreading and retention of vaginal formulations in post-menopausal women as assessed by gamma scintigraphy," Pharm. Res. 14(8):1073-78 (1997).

Brusset, A., "Comparative Phamacokinetic Study of Fentanyl and Sufentanil after Single High-Bolus Dosts," Clin. Drug Invest. 18(5):377-389 (Nov. 18, 1999).

Burgalassi, et al., "A novel mucoadhesive buccal drug delivery system," Proc. 1st World Meet. APGI/APV Budapest, 911 p. 839-71 (1995).

CA Notice of Allowance issued Aug. 30, 2010 in Appln. No. 2,511,974.

Camu, F. "Postoperative Analgesic Effects of Three Demand-Dose Sizes of Fentanyl Administered by Patient-Controlled Analgesia," Anesth. Analg. 87:890-895 (1998).

Chen, C., "Some pharmacokinetic aspects of the lipophilic terfanadine and zwitterionic fexofenadine in humans.", Drugs R D. 2007; 8(5):301-14.

Cherny, N., et al., "Medikamentose Therapie von Tumorschmerzen," Der Schmerz, 9:3-19 (1995).

Chien, et al., (eds) Nasal Systemic drug Delivery, Dekker, New York, 1989 (Front page and publication details) (too voluminous to include).

Cleary, J.F., "Pharmacokinetic and Pharmacodynamic Issues in the Treatment of Breakthrough Pain," Seminars in Oncology, 24(5)(16):S16-13 to S16-19 (1997).

Communication dated May 9, 2005 from the Norwegian Patent Office in NO Application No. 19995021.

Communication Under Rule 51(4) EPC Issued Jul. 23, 2003 in EP Application No. 98917414.9.

Dale. O. et al., "Nasal administration of opioids for pain management in adults", Acta Anaesthesiol. Scand. 46:759-770 (2002).

(56) References Cited

OTHER PUBLICATIONS

Decision and Grant of Patent dated Jan. 10, 2008 in GE Application No. AP2004009831.
Decision of Grant Mar. 12, 2007 in EA Appln. 200501105; Letters Patent and granted patent.
Decision of Grant dated Sep. 18, 2007 in UZ Application No. IAP20050288.
Decision of Grant dated Sep. 29, 2008 in UA Application No. 200507799.
Dongowski et al., "Interactions between food components and drugs. Part 4: Influence of pectins and bile salts on propanolol absorption", International Journal of Pharmaceutics, 144:233-239 (1996).
Eichner, H. et al., "Nasal secretions—diagnostic possibiities—normal values," Laryngologie Rhinologie Otologie, (1983) vol. 62, No. 12, pp. 561-565. (Abstract only).
Final Rejection dated Jan. 28, 2009 in KR Application No. 10-2005-7012821.
Finkel, Julia, C., et al., "The Effect of Intranasal Fentanyl on the Emergence Characteristics After Sevoflurane Anesthesia in Children Undergoing Surgery for Bilateral Myringotomy Tube Placement," Anesth. Analg. 92:1164-1168 (2001.
Finkel, Julia, et al., Anesthesiology Abstracts of Scientific Papers Annual Meeting, Abstract No. 1252 (2002).
Galinkin, Jeffrey L., et al., Anesthesiology Abstracts of Scientific Papers Annual Meeting, Abstract No. 1253 (2002).
Galinkin, Jeffrey L, et al., "Blood Levels of Fentanyl Adter Intranasal Administration in Children Undergoing Bilatierial Myringotomy and Tube Placement (BMT)," ASA Abstracts, Anesthesiology, 91(3A):A1279 (1999).
Galinkin, Jeffrey L., M.D., et al. "Use of Intranasal Fentanyl in Children Undergoing Myringotomy and Tube Placement during Halothane and Sevoflurane Anesthesia,"Anesthesiology 93:1378-1383 (2000).
Galinkin, Jeffrey L, M.D., et al., Reply to Ueda above, 95:813 (2001).
Garnier et al., Selectivity and cooperativity in the binding of calcium ions by pectin, carbohydrate research, 256 (1994) 71-81.
Garnier, C. et al., "Phase diagrams of pectin-calcium systems: Influence of pH, ionic strength, and temperature on the gelation of pectins with different degrees of methylation," Carbohydrate Research, 240 © (1993) pp. 219-232, Elsevier Science Publishers, B.V., Amsterdam.
Geigy Scientific Tables, vol. 1, Eighth Edition, © 1981 CIBA-GEIGY Limited, Basel Switzerland, 3 pages.
Handbook of Pharmaceutical Excipients, pp. 386-388, A.H. Kippe (ed.), 3rd edition, Pharmaceutical Press, London, UK, 2000.
Hermens, Walter A.J.J., et al., "The In Vitro Effect of Morphine, Fentanyl and Sufentanil on Coliary Beat Frequency of Human Nasal Epithelial Tissue," Acta Pharm. Technol. 33(2):88-90 (1997).
Illum & Fisher, "Inhalation Delivery of Therapeutic Peptides and Proteins", (Adjei & Gupta, eds.) pp. 135-184, Marcel Dekker, Inc.: New York (1997).
Illum, et al. "Bioadhesive Microspheres as a Potential Nasal Drug Delivery System", Int. J. Pharm. 39:189-99 (1987).
Illum, et al. "Chiitosan as a novel nasal delivery system for peptide drugs," Pharm. Res. 11(8):1186-89 (1994).
Int'l Search Report dated Sep. 9, 1998 in US Application No. PCT/GB98/01147.
Int'l Search Report Issued Aug. 4, 2004 in Int'l Application No. PCT/GB2004/00057.
Zeppetella, Giovambattista, "An Assessment of the Safety, Efficacy, and Acceptability of Intranasal Fentanyl Citrate in the management of Cancer-Related Breakthrough Pain: A Pilot Study," Journal of Pain and Symptom Management, 20(4):253-258 (Oct. 2000).
Zeppetella, Giovambattista, "Nebulized and intranasal fentanyl in the mangement of cancer-related breakthrough pain," Palliative Medicine 14:57-58 (2000).
Office Action Issued Apr. 6, 2010 in JP Application No. 2008-257989.
Communication dated Oct. 26, 2010 from the Polish Patent Office in PL Application No. P-377823.
Office Action Issued Jan. 27, 2011 in U.S. Appl. No. 12/047,388.
Order of Allowance Issued Nov. 1, 2010 in KR Application Ser. No. 10-2009-7010700.
Office Action Issued May 29, 2009 in KR Application No. 2008-257989.
Office Action Issued Oct. 4, 2010 in U.S. Appl. No. 11/562,173.
Office Action Issued Mar. 1, 2011 in JP Application No. 2008-257989.
Office Action Issued Mar. 22, 2011 in the Brazilian Official Gazette 2098.
Office Action Issued Mar. 1, 2011 in JP Application No. 2006-500187.
Office Action Issued Mar. 10, 2011 in PL Application No. P-377823.
Office Action issued Sep. 29, 2011 in U.S. Appl. No. 12/047,388.
Eriksen et al, "The systemic availability of buprenorphine administered by nasal spray," Journal of Pharmacy and Pharmacology, vol. 41, pp. 803-805 (1989).
Decision of Patent issued Aug. 8, 2011 in JP Application No. 2006-500187.
Office Action issued Apr. 25, 2012 in U.S. Appl. No. 13/078,575.
Barnett et al, "Head-Turning Induced by Electrical Stimulation of the Caudate Nucleus and Its Antagonism by Anti-Parkinson Drugs," The Journal of Pharmacology and Experimental Therapeutics, vol. 194, No. 2, pp. 296-302 (1975).
U.S. Appl. No. 13/541,325 by Watts, filed Jul. 3, 2012.
Talukdar et al, International Journal of Pharmaceutics, vol. 129, pp. 233-239 (1996).
Lindhardt et al, International Journal of Pharmaceutics, vol. 217, pp. 121-126 (2001).
Lindhardt et al, International Journal of Pharmaceutics, vol. 205, pp. 159-163 (2000).
The Merck Index, 13th Ed., Entry 6551 (2001).
Martindale: The Extra Pharmacopoeia, 31st Ed., Edited by James E F Reynolds, pp. 42-45 (1996).
Patent Abstract of Japan, vol. 2000, No. 11, Jan. 3, 2001.
Semde et al, "Leaching of pectin from mixed . . . ", International Journal of Pharmaceutics, vol. 174, pp. 233-241 (1998).
Cassidy et al, "Controlled Buccal Delivery . . . ", Journal of Controlled Release, vol. 25, pp. 21-29 (1993).
Hussain et al, "Nasal absorption of naloxone and buprenorphine in rats", International Journal of Pharmaceutics, vol. 21, pp. 233-237 (1984).
Reich et al, "Tonicity, Osmoticity, Osmolality and Osmolarity", Remington: The Science and Practice of Pharmacy, 19th Ed., vol. 1, pp. 613-615 (1995).
Naim, "Solutions, Emulsions, Suspensions and Extracts", Remington: The Science and Practice of Pharmacy, 19th Ed., vol. 2, pp. 1495-1496 and 1502 (1995).
Verma et al, "Modulatory role of D-1 and D-2 dopamine receptor subtypes in nociception in mice", Journal of Psychopharmacology, vol. 7, No. 3, pp. 270-275 (1993).
Office Action and English translation dated May 14, 2009 in JP Application No. 2003-577852.
Ventafridda, Psychopharmacology, vol. 95, pp. S44-S49 (1988).
Office Action issued Feb. 9, 2012 in IL Application No. 169480.
Office Action issued Mar. 20, 2012 in IN Application No. 1131/DELNP/2008.
Office Action issued Aug. 3, 2012 in EP Application No. 04701381.8.
Extended Search Report and Written Opinion issued Mar. 7, 2012 in EP Application No. 11185114.3.
Notice of Allowance issued Jul. 4, 2012 in PL Application No. P-377823.
Notice of Allowance and Certificate of Grant issued Dec. 9, 2011 in JP Application No. 2008-257989.
Office Action issued Jun. 14, 2012 in JP Application No. 2010-071698.
Office Action Issued Jul. 11, 2006 in EA Application No. 200501105.
Office Action Issued Jul. 12, 2007 in UZ Application No. IAP20050288 (regarding claims).
Office Action issued Jul. 20, 2010 in IL Appl. No. 169480.
Office Action Issued Jul. 6, 2001 in UK Application No. GB9924123.4.
Office Action Issued Aug. 10, 2005 in U.S. Appl. No. 10/196,590.

(56) References Cited

OTHER PUBLICATIONS

Office Action Issued Sep. 12, 2008 in U.S. Appl. No. 10/196,590.
Office Action Issued Sep. 19, 2002 in EP Application No. 98917414.9.
Office Action Issued Sep. 26, 2007 in U.S. Appl. No. 10/196,590.
Opposition against counterpart European Patent 9 975 367, dated Dec. 21, 2004.
Oral, U. et al., "Intranasal fentanyl administratiion for postoperative pain relief," Br. J. Anesth., 74 Suppl. 1, 139 (A.458) (1995).
Ozbek, Hayri, et al., "Comparison of the Effects of Intranasal and Intravenous Fentanyl Administration on Postoperative Pain Relief," Turk Anest Rean Cem Mecmuast 25:467-470 (1997).
Paech M.J., et al., "A new formulation of nasal fentanyl spray for postoperative analgesia: a pilot study," Anaesthesia, 58:740-744 (2003).
Peng, P.W.H., et al., A review of the Use of Fentanyl Analgesia in the Management of Acute Pain in Adult, Anesthesiology, 90:576-599 (1992).
Physician's Desk Reference, 54th edition, pp. 405-409, Medical Economics Company, Montvale, NJ 2000.
Pilnik et al., Gelling Agents (Pectins) From Plants for the Food Industry, Advances in Plant Cell Biochemistry and Biotechnology, vol. 1, pp. 219-270 (1992).
Popovici & Szasz, "Mucoadhesive gel with polyuranides for endonasal administration," *Buccal and nasal administration as alternatives to parental administration, Minutes of a European Symposium* (Duchene, ed.) pp. 292-296, Sante Paris, France (1992).
Potts, et al., "In vivo determination of a oesophageal retention of smart hydrogel" Proceed. Intern. Symp. Control Rel. Boiact. Mater. 24:335-36 (1997).
Preliminary Grant dated Jun. 27, 2007 in GE Appln. AP2004009831.
Ralley, Fiona E., "Intranasal opiates: old route for new drugs," Can. J. Anaeth., 36:5 pp. 491-493 (1989).
Re-exam result and dismissal of amendment dated Jun. 25, 2009 in KR Application No. 10-2005-7012821.
Result of Trial dated Dec. 30, 2009 in Kr Application No. 10-2005-7012821.
Robertson, Sheilah A., et al., "Efficacy of the Intranasal Route for Administration of Anesthetic Agents to Adult Rabbits," Laboratory Animal Science, 44(2):159-165 (Apr. 1994).
Rolin, et al., "Pectin", *Industrial Gums*, Academic Press: New York pp. 257-93 (1993).
Roy, S.D., "Solubility Behavior of Narcotic Analgesics in Aqueous Media: Solubilities and Dissociation Constants of Morphine, Fentanyl, and Sufentanil," Pharmaceutical research, 6(2): 147-151 (1989).
Rozier, A. et al,. Gelrite® "A novel, ion-activated,in-situ gelling polymer for ophthalmic vehicles, Effect on bioavailability of timolol," International Journal of Pharmaceutics, 57 (1989) pp. 163-168, Elsevier Science Publisher, B.V.
Schwagmeier, R. "Patientenakzeptanz gegenuber der patientenkontrollierten intranasalen Analgesic (PCINA)"Anaesthesist, 45: 231-234 (1996)—(C) Springer-Vertag 1996.
Search report issued May 31, 2006 in GE Application No. AP2004008931.
Sebel, P.S., et al., "Transdermal Absorption of Fentanyl and Sufentanil in Man," Eur. J. Clin. Pharmacol. 32:529-531 (1987).
Shende, D., et al., "Comparison of Oral Midazolam with Intra-Nasal Midaxolam, Intra-Nasal Fentanl & Combination of Intra-Nasal Fentanyl and Midazolam in Children Undergoing Efective Eye Surgery," Anesthesia & Analgesia, 94:S250 (2002).
Smart, et al., "An in-vitro investigation of mucosa-adhesive materials for use in controlled drug delivery," J. Pharm. Pharmacol. 36(5):295-99 (1984).
Soane, et al., Int. J. Pharm. 178, 55-65, 1999.
Stanley, Theodore H., et al., "Novel Delivery Systems: Oral Transmucosal and Intranasal Transmucosal," Journal of Pain and Symptom Management, 7(3):163-171 (Apr. 1992).
Streisand, J.B., "Absorption and Bioavailability of Oral Transmucosal Fentanyl Citrate," Anesthesiology, 75:223-229 (1991).
Streisand, J.B., et al., "Buccal Absorption of Fentanyl is pH-dependent in Dogs," Anesthesiology, 82(3):759-764 (1995).
Streisand, J.B., et al., "Newer drug delivery systems," Current Anaesthesia and Critical Care, 6:113-120 (1995).
Striebel, et al., Brit. J. Anaesthesia, 96 Suppl. 1, pp. 108 & 109 (1993).
Striebel, H. W., M.D., "Postoperative Pain Managemetn by Intranasal Demand-adapted Fentanyl Titration," Anesthesiology, 77:281-285 (1992).
Striebel, H.W., "Die intranasale Opioidgabe zur therapie von Schmerzenn—ein neuer Applikationsweg," Anasthesiologi & Intensivmedizen, 3(37):128-134 (1996)—(in German).
Striebel, H.W., "Intranasal fentanyl titration for posoperative pain management in an unselected population," Brit. J. Anaesthesia, 48:753-757 (1993).
Striebel, H.W., "Patient-Controlled Intranasal Analesia: A Method for Noninvasive Postoperative Pain Management," Anesth. Analg., 83:548-551 (1996).
Striebel, H.W., "Patient-Controlled Intranasal Analgesia (PCINA) for the Management of Postoperative Pain: a Pilot Study," Journal of Clinical Anesthesia, 8:4-8 (1996).
Striebel, H.W., "Pharmakokinetische Studie zur intranaselen Gabe von Fentanyl," Originalien—Der Schmerz, 122-125 (1993) (English abstract shown).
Striebel, H.W., et al., "Ein neues Gerat zur patientenkontrollierten intranasalen Analgesie," Der Schmerz, 9:84-88 (1995).
Striebel, H.W., et al., "Intranasales Fentanyl zur therapie akuter Schmerzspitzen bei Karzinompatienten," Der Schmerz, 7:174-177 (1993).
Striebel, H.W.,M.D., Ph.D., DEAA, et al., "Non-invasive methods for PCA in pain management,"Acute Pain, 2 (1):36-40 (1999).
The Merck Index, 12th Edition, Publ. By Merck Reserach Laboratories, Div. Of Merck & Co., Inc., pp. 679-680 (1996).
The Merck Index: An Enclyclopedia of Chemicals, Drugs, and Biologicals, Twelfth Edition, Merck & Co., Inc., Whitehouse Station, N.J., 1996, 2 pages.
The Proctor & Gamble Company, "Complete Specification, Section 10—A Nasal Spray Containing an Intranasal Steroid and an Antihistamine," 2827/DEL (1996).
Toussaint, et al., Can. J. Anesth., 47, 299-302, 2000.
Ueda, Wasa, M.D., "Rhinorrhea by Nasal Fentanyl," Anesthesiology 95:812-813 (2001).
UK Application No. GB9924123.4 Notification of Grant of Patent No. GB2340039, Jan. 8, 2002.
Voragen et al,., Food Polysaccharides and The Applications, Chapter 10 Pectins, pp. 287-339 (1995).
Walter, "Analytical and graphical methods for pectin," *The Chemistry and Technology of Pectin*, pp. 189-225, Academic Press: New York (1991).
Ward, M., et al., "A comparison of patient-controlled analgesia administered by the intravenous or intranasal route during the early postoperative period," Anesthesia 57:48-52 (2002).
Wong, P., et al., "Intranasal fentanyl for postoperative analgesia after elective Caesarean section," Anaesthesia, 58:818-819 (2003).
Worsley, M.H., "Inhaled fentanyl as a method of analgesia," Anaesthesia, 45:449-451 (1990).
Xiaobin, W., et al., "Observation of the effects of a small dose of fentanyl nasal spray for pain alleviation after surgery," Journal of Luzhou Medical College, 21(2):149-150 (1998).
Yanli, B., "Clinical observation of combination of Fentanyl and Ketamine by nasal spray in induced abortion," Chinese Community Doctors, 35-36 (2003).
Yee, J.B., et al., "Novel Drug Delivery Systems," Headache Quarterly, 5:2, pp. 128-134 (1994).
Younge, P.A., "A prospective randomized pilot comparison of intranasal fentanyl and intramuscular morphine for analgesia in children presenting to the emergency department with clinical fractures." Emergency Medicine, 11:90-94 (1999).

(56) References Cited

OTHER PUBLICATIONS

Zandsberg, Shaul, M.D., et al. "Nonconventional Drug Administration in Anesthesia," New Drugs in Anesthesia, Part II, Anesthesiology Clinics of North America, 12(1):17-38 (Mar. 1994).
Isik, G., et al., "The Effects of Intransal Fentanyl and Alfentanyl in Postoperative Pain relief," Agri Dergisi, CCit:7, Sayi 3, pp. 18-22 (1995).
Jaffe, A.B., et al., "Rats self-administer sufentanil in aerosol form," Psychopharmacology 99:289-293 (1989).
Japanese Patent Application No. 10-545285, Notification of Reasons for Refusal, dated Dec. 11, 2007.
Joly, L. M., M.D., et al., "Patient-Controlled Intranasal Analgesia", Anesth. Analg. 85:463-466 (1997).
Kahveci, Kadriye Turkay, et al., "The Effects of Intranasal Midzaolam, Ketamine, Al-fentanil and Fentanyl on Children Premedication," Turk. Anest. Rean Mecmuasi 25:299-304 (1997) (English language Summary Only).
Kenaan, C.A., M.D., et al., "Pharmacodynamics and Intubating Conditions of Cisatracurium in Children During Halothane and Opiod Anesthesia," Journal of Clinical Anesthesia, 12:173-176 (2000).
Kondo, T., et al., "Effects of Cyclodextrins on Nasal Absorption and Analogesic Activity of Opiods in Rats", Proceedings of the Eighth International Symposium on cyclodextrins, 387-390 (1996).
L Mitterhauszerova et al., "Interaction of Aminopyrine, 4-Aminoantipyrine, Nicotine Amie, and P-Aminosalicylate with Pectic Acid", Pharmacology Magazine, Issue L11, pp. 501-508 (1983).
Latasch, Leo, M.D., Ph.D., et al., "Nasal Fentanyl Versus Sufentanil for Postoperative Analgesia in Gynecological Patients," Anesthesiology Abstracts of Scientific Papers Annual Meeting, Abstract No. A-491 (2003).
Letters Patent dated Dec. 30, 2008 in CA Application No. 2,282,506.
Letters Patent dated Mar. 28, 2002 in AU Application No. 70647/98.
Letters Patent dated May 6, 2008 in GE Application No. AP2004009831.
Lim, Stephen (CB), et al., "Pharmacokinetics of Nasal Fentanyl," Journal of Pharmacy Practice and research 33:59-63 (2003).
Majushree, et al., Can. J. Anesth. 49, 190-193, 2002.
Martin, A.N., Physical pharmacy: physical chemical principles in the pharmaceutical sciences, 4th Edition, pp. 498, 499 (1993).
Martindale, The Extra Pharmacopoeia, Edited by James E.F. Reynolds, pp. 43-46 (1996).
Martindale, The Extra Pharmocopoeia, 31st Ed., The Pharmaceutical Press: London (1996).
McCaffery, M., et al., "How to choose the best route for an opiod," Nursing 2000, 30(12):34-40 (2000).
Mi, W.D., et al., "Hypnotic endpoints vs. the bispectral index, 95% spectral edge frequency and median frequency during propofol infusion with or without fentanly,"European Journal of Anesthesiology, 16:47-52 (1999).
Mizutani, A., et al., "Effect of Nasal Midazolam with Fentanly for Preinduc tion of Anesthesia and Postoperative Analgesia in Pediatric Patients," The Journal of Japan Society for Clinical Anesthesia, 15(5) 398-401 (Jun. 1995).
Niels Mygind, M.D., "Nasal Allergy," Blackwell Scientific Publications, ã1978, 3 pages.
Notice of Acceptance dated Nov. 5, 2001 in AU Application No. 70647/98.
Notice of Acceptance dated May 24, 2001 in NZ Application No. 337289.
Notice of Acceptance dated Jul. 7, 2008 in NZ Application No. 541018.
Notice of Allowance dated Apr. 9, 2002 for U.S. Appl. No. 09/402,976, 3 pages.
Notice of Allowance Issued Apr. 10, 2008 in CA Application No. 2,282,506.
Notice of Allowance Issued Apr. 19, 2006 in NO Application No. 19995021.
Notification of Grant Issued Jan. 29, 2007 in EA Appln. 200501105.
O'Neil, G. "Preliminary Clinical Use of a Patient-Controlled Intranasal Analgesia (PCINA) Device, "Anaesth. intens. Care, 25:408-412 (1997).
O.B. Shipunova et al., "Immobilization of isoniazid on pectin compounds", Izvestiya Akademii Nauk Kazakhskoi SSR, Seriya Khimicheskya, (2), pp. 83-88 (1990).
Oechslein, et al. "Nasal delivery of octreotide: Absorption enhancement by particulate carrier systems," Int. J. Pharm. 139:25-32 (1996).
Office Action issued Jun. 25, 2009 in KR Application No. 10-2009-7010700.
Office Action issued Jan. 14, 2010 in PL Application No. P-377823.
Office Action Issued Jan. 25, 2008 in MX Application No. PA/a/2005/007333.
Office Action Issued Jan. 25, 2008 in U.S. Appl. No. 10/196,590.
Office Action Issued Jan. 3, 2006 in NO Applicatiion No. 19995021.
Office Action Issued Jan. 31, 2008 in NZ Application No. 541018.
Office Action Issued Jan. 4, 2010 in U.S. Appl. No. 10/196,590.
Office Action Issued Oct. 12, 2001 in UK Application No. GB9924123.4.
Office Action Issued Oct. 12, 2006 in U.S. Appl. No. 10/753,628.
Office Action Issued Oct. 14, 2009 in EP Application No. 04701381.8.
Office Action Issued Oct. 23, 2007 in MX Application No. PA/a/2005/007333.
Office Action Issued Oct. 23, 2009 in AU Application No. 2004204381.
Office Action Issued Oct. 26, 2006 in UZ Application No. IAP20050288.
Office Action Issued Nov. 19, 1999 in NZ Application No. 337289.
Office Action Issued Nov. 2, 2007 in U.S. Appl. No. 10/753,628.
Office Action Issued Nov. 24, 2006 in CN Application No. 200480002000.x.
Office Action Issued Nov. 29, 2000 in UK Application No. GB9924123.4.
Office Action issued Nov. 9, 2007 in CN Application No. 200480002000.x.
Office Action Issued Dec. 11, 2007 in JP Application No. 10-545285.
Office Action Issued Dec. 3, 2001 in U.S. Appl. No. 09/402,976.
Office Action Issued Feb. 1, 2008 in CA Application No. 2,282,506.
Office Action Issued Feb. 16, 2010 in CA Application No. 2,511,974.
Office Action Issued Feb. 4, 2008 in IN Application No. 2991/DELNP/2005.
Office Action issued Feb. 6, 2007 in GE Application No. AP2004008931.
Office Action Issued Mar. 13, 2001 in NZ Application No. 337289.
Office Action Issued Mar. 14, 2007 in U.S. Appl. No. 10/196,590.
Office Action Issued Mar. 16, 2010 in JP Appln. No. 2006500187.
Office Action Issued Mar. 17, 2006 in U.S. Appl. No. 10/196,590.
Office Action issued Mar. 22, 2007 in IN Application No. 2991/DELNP/2005.
Office Action issued Mar. 31, 2009 in CA Application No. 2,511,974.
Office Action Issued Mar. 9, 2010 in AU Application No. 2004204381.
Office Action Issued Apr. 10, 2007 in UZ Application No. IAP20050288.
Office Action Issued Apr. 12, 2006 in CA Application No. 2,282,506.
Office Action issued Apr. 20, 1998 in KR Appln. No. 2008-257989.
Office Action Issued Apr. 26, 2001 in NZ Application No. 337289.
Office Action Issued Apr. 26, 2007 in NZ Application No. 541018.
Office Action Issued Apr. 30, 2010 in U.S. Appl. No. 12/047,388.
Office Action Issued Apr. 4, 2008 in UA Application No. 200507799.
Office Action Issued Apr. 5, 2005 in NO Application No. 19995021.
Office Action Issued Apr. 6, 2009 in IL Application No. 169480.
Office Action Issued May 1, 2008 in UA Application No. 200507799.
Office Action Issued May 2, 2001 in AU Application No. 70647/98.
Office Action Issued May 2, 2007 in U.S. Appl. No. 10/753,628.
Office Action Issued May 25, 2010 in KR Appln. No. 10-2009-7010700.
Office Action Issued May 28, 2009 in AU Application No. 2004204381.
Office Action Issued May 8, 2001 in U.S. Appl. No. 09/402,976.
Office Action Issued May 9, 2007 in CA Application No. 2,282,506.
Office Action Issued Jun. 10, 2008 in JP Application No. 10-545285.

(56) References Cited

OTHER PUBLICATIONS

Office Action Issued Jun. 17, 2009 in U.S. Appl. No. 10/196,590.
Office Action Issued Jun. 24, 2008 in KR Application No. 10-2005-7012821.
Office Action issued Jun. 25, 2010 in AU Appln. No. 2004204381.
Office Action Issued Jun. 9, 2009 in JP Application No. 2008-257989.
Opposition against counterpart European Patent 9 975 367, dated Dec. 21, 2004.
Office Action issued Dec. 24, 2012 in the reexamination of corresponding AU Patent No. 741847.
"Fentanyl 25-pg/0.1-mL Nasal Spray," International Journal of Pharmaceutical Compounding,, 4(1)57 (Jan./Feb. 2000).
Borland, M.D., et al., "Intranasal fentanyl reduces acute pain in children in the emergency department: A safety and efficacy study," Emergency Medicine 14:275-280 (2002).
British Search Report Issued Jan. 27, 2004 in GB Application No. GB0300531.1 (cited in parent U.S. Appl. No. 10/753,628.
Brusset, A., "Comparative Pharmacokinetic Study of Fentanyl and Sufentanil after Single High-Bolus Dosts," Clin. Drug Invest. 18(5):377-389 (Nov. 18, 1999).
Chen, C., "Some pharmacokinectic aspects of the lipophilic terfanadine and zwitterionic fexofenadine in humans.", Drugs R D 2007; 8(5):301-14.
Cherny, N., et al., "Medikamentose Therapie von Tumorschmerzen,"Der Schmerz, 9:3-19 (1995).
Eichner, H. et al., "Nasal secretions—diagnostic possibilities—normal values," Laryngologie Rhinologie Otologie, (1983) vol. 62, No. 12, pp. 561-565. (Abstract only).
Galinkin, Jeffrey L., et al., "Blood Levels of Fentanyl Adter Intranasal Administration in Children Undergoing Bilateral Myringotomy and Tube Placement (BMT)," ASA Abstracts, Anesthesiology, 91(3A):A1279 (1999).
Galinkin, Jeffrey L., M.D., et al., Reply to Ueda above, 95:813 (2001).
Hermens, Walter A.J.J., et al., "The In Vitro Effect of Morphine, Fentanyl and Sufentanil on Coliary Beat Frequency of Human Nasal Epithelial Tissue,"Acta Pharm. Technol. 33(2):88-90 (1997).
Kahveci, Kadriye Turkay, et al., "The Effects of Intranasal Midzaolam, Ketamine, Al-fentanil and Fentanyl on Children Premedication,"Turk. Anest. Rean Mecmuasi 25:299-304 (1997) (English language Summary Only).
Kenaan, C.A., M.D., et al., "Pharmacodynamics and Intubating Conditions of Cistracurium in Children During Halothane and Opiod Anesthesia," Journal of Clinical Anesthesia, 12:173-176 (2000).
L. Mitterhauszerova et al., "Interaction of Aminopyrine, 4-Aminoantipyrine, Nicotine Amie, and P-Aminosalicylate with Pectic Acid", Pharmocology Magazine, Issue L11, pp. 501-508 (1983).
Latasch, Leo, M.D., Ph.D., et al., "Nasal Fentanyl Versus Sufentanil for Postoperative Analgesia in Gynecological Patients,"Anesthesiology Abstracts of Scientific Papers Annual Meeting, Abstract No. A-491 (2003).

Lim Stephen (CB), et al., "Pharmacokinetics of Nasal Fentanyl," Journal of Pharmacy Practice and research 33:59-63 (2003).
Mi, W.D., et al., "Hynotic endpoints vs. the bispectral index, 95% spectral edge frequency and median frequency during propofol infusion with or without fentanly,"European Journal of Anesthesiology, 16:47-52 (1999).
Niels Mygind, M.D., "Nasal Allergy," Blackwell Scientific Publications, © 1978, 3 pages.
O'Neil, G. "Preliminary Clinical Use of a Patient-Controlled Intranasal Analgesia (PCINA) Device," Anaesth. intens. Care, 25:408-412 (1997).
Office Action Issued Jan. 3, 2006 in NO Application No. 19995021.
Office Action Issued Oct. 12, 2001 in UK Application No. GB9924123.4
Office Action issued Feb. 6, 2007 in GE Application No.AP2004008931.
Office Action issued Mar. 22, 2007 in IN Application No 2991/DELNP/2005.
Office Action issued Sep 29, 2011 in U.S. Appl. No. 12/047,388.
Eriksen et al. "The systemic availability of buprenorphine administered by nasal spray,"Journal of Pharmacy and Pharmacology, vol. 41, pp. 803-805 (1989).
Semde et al. "Leaching of pectin from mixed . . . ", International Journal of Pharmaceutics, vol. 174, pp. 233-241 (1998).
Talukdar et al. International Journal of Pharmaceutics, vol. 129, pp. 233-239 (1996).
Verma et al. "Modulatory role of D-1 and D-2 dopamine receptor subtypes in nociception in mice", Journal of Psychopharmacology, vol. 7, No. 3, pp. 270-275 (1993).
Chetoni, et al., "veicoli oftalmici mucoadesivi: studio preliminare della farmacocinetica oculare 'In vivo'," Boll. Chem Farm. 135:147-149 (Feb. 1996).
Granted Patent in NZ Application No. 541018, dated Nov. 13, 2008.
Eichner et al. (Diagnostic value of nasal secretions, current state: normal values) Laryngol Rhinol Otol (Stuttg) (Dec. 1983).
EP Application No. 98917414.9 Communications regarding opposition including decision of the Opposition Division to maintan the patent as granted, dated Dec. 21, 2004.
Grant of CN Patent No. ZL200480002000.x, dated Oct. 8, 2008.
International Preliminary Report on Patentability in Int'l Application No. PCT/GB98/01147, dated May 18, 1999.
NZ Application No. 337289 Letters Patent and Patent, dated Oct. 9, 2001.
Striebel, H.W., et al., "Patientenkontrollierte intranasale Analgesie (PCINA) zur Therapie postoperativer Schmerzen-eine Pilotstudie," Anaesthesist (Suppl. 1) 43:S215 (FV34.6) (1994).
Volles, D.G., et al., "Pharmacokinetic Considerations" (Jan. 1999).
Zhou, et al., Intranasal Mucocilliary Clearance of Putative Broadhesive Polymer Gels (1996).
Office Action issued Apr. 24, 2013 in EP Application No. 04 701 381.8.
Re-Examination Report issued Mar. 21, 2013 in AU Patent No. 741847.

METHOD OF MANAGING OR TREATING PAIN

CROSS-REFERENCE TO RELATED APPLICATION

This application is a continuation of U.S. patent application Ser. No. 12/047,388, filed Mar. 13, 2008, now U.S. Pat. No. 8,216,604, issued Jul. 10, 2012, which in turn is a division of U.S. patent application Ser. No. 10/753,628, filed Jan. 8, 2004, now abandoned, the disclosures of each of which are hereby incorporated herein by reference in their entirety.

BACKGROUND OF THE INVENTION

This invention relates to pharmaceutical compositions for the intranasal administration of fentanyl.

The nasal route of drug delivery can afford rapid onset of action and convenience to patients and/or care giver. In particular, this route can provide rapid absorption of drugs into the blood circulation. In some cases absorption of almost the whole dose can be achieved and the pharmacokinetics can be similar to intravenous administration. Such rapid and effective drug delivery can be useful in the treatment of crisis situations such as pain, including breakthrough pain, headache and migraine (Nasal Systemic Drug Delivery, Chien et al. (eds), Dekker, New York, 1987).

Fentanyl (N-(1-phenethyl-4-piperidyl)propionanilide) is a potent opioid analgesic and may be used in the treatment of severe acute and chronic pain.

It has been reported that fentanyl is rapidly and well absorbed from the nasal cavity (Striebel et al., Brit. J. Anaesthesia, 96, suppl 1, 108, 1993). In addition, the effectiveness of intranasal fentanyl in providing analgesia in patients has been demonstrated in a number of studies (for example Striebel et al., Brit. J. Anaesthesia, 96, suppl 1, 108 and 109, 1993; Striebel et al., Anaesthesia, 48, 753-757, 1993; Majushree et al., Can. J. Anesth., 49, 190-193, 2002; Toussaint et al., Can. J. Anesth., 47, 299-302, 2000). In all of these studies the intranasal administration of fentanyl appears to have been achieved by dropping or spraying a commercially available injection formulation into the nose (SUBLIMAZE®, from Janssen). The commercially available injection formulation of fentanyl contains 0.05 mg of fentanyl, in the form of the citrate salt, in 1 ml of sodium chloride solution and necessitates the intranasal administration of a large volume of liquid in order to provide a therapeutically effective dose of drug.

Fentanyl is also currently available in a transdermal patch and a transmucosal lozenge. The transdermal patch (for example DUROGESIC® from Janssen) provides a steady concentration of fentanyl in plasma over a prolonged period and is not suitable for the rapid relief of severe pain, such as breakthrough pain associated with terminal illness or acute pain associated with trauma or following surgery. The transmucosal lozenge (ACTIQ®, Cephalon Inc) is used in the treatment of breakthrough pain and is available in a number of dose strengths ranging from 0.2 to 1.6 mg. The absorption of fentanyl from the transmucosal formulation is relatively slow. Times to achieve the peak plasma concentration ($T_{max}$) of from 20 to 480 minutes have been reported (pp. 405-409, Physician's Desk Reference, 54th edition, Medical Economics Company, Montvale, N.J., 2000).

Thus, there remains a need for alternative means for the delivery of fentanyl, for example via the intranasal route.

The listing or discussion of a prior-published document in this specification should not necessarily be taken as an acknowledgement that the document is part of the state of the art or is common general knowledge.

BRIEF SUMMARY OF THE INVENTION

The present invention provides a composition suitable for the intranasal administration of fentanyl that overcomes one or more of the problems described above, and a method of using it to treat or manage pain in a subject.

More specifically, the present invention relates to a method of treating or managing pain by intranasally administering to an animal in need thereof in an amount to effectively treat or manage pain a pharmaceutical composition comprising an aqueous solution of fentanyl or a pharmaceutically acceptable salt thereof in an amount to effectively treat or manage pain and a pectin having a degree of esterification (DE value) of less than 30%, provided that the composition is substantially free of divalent metal ions;

wherein the animal administered the composition is provided with a peak plasma concentration of fentanyl ($C_{max}$) that is from 10 to 80% of that achieved using a simple aqueous solution of fentanyl administered intranasally at an identical fentanyl dose.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
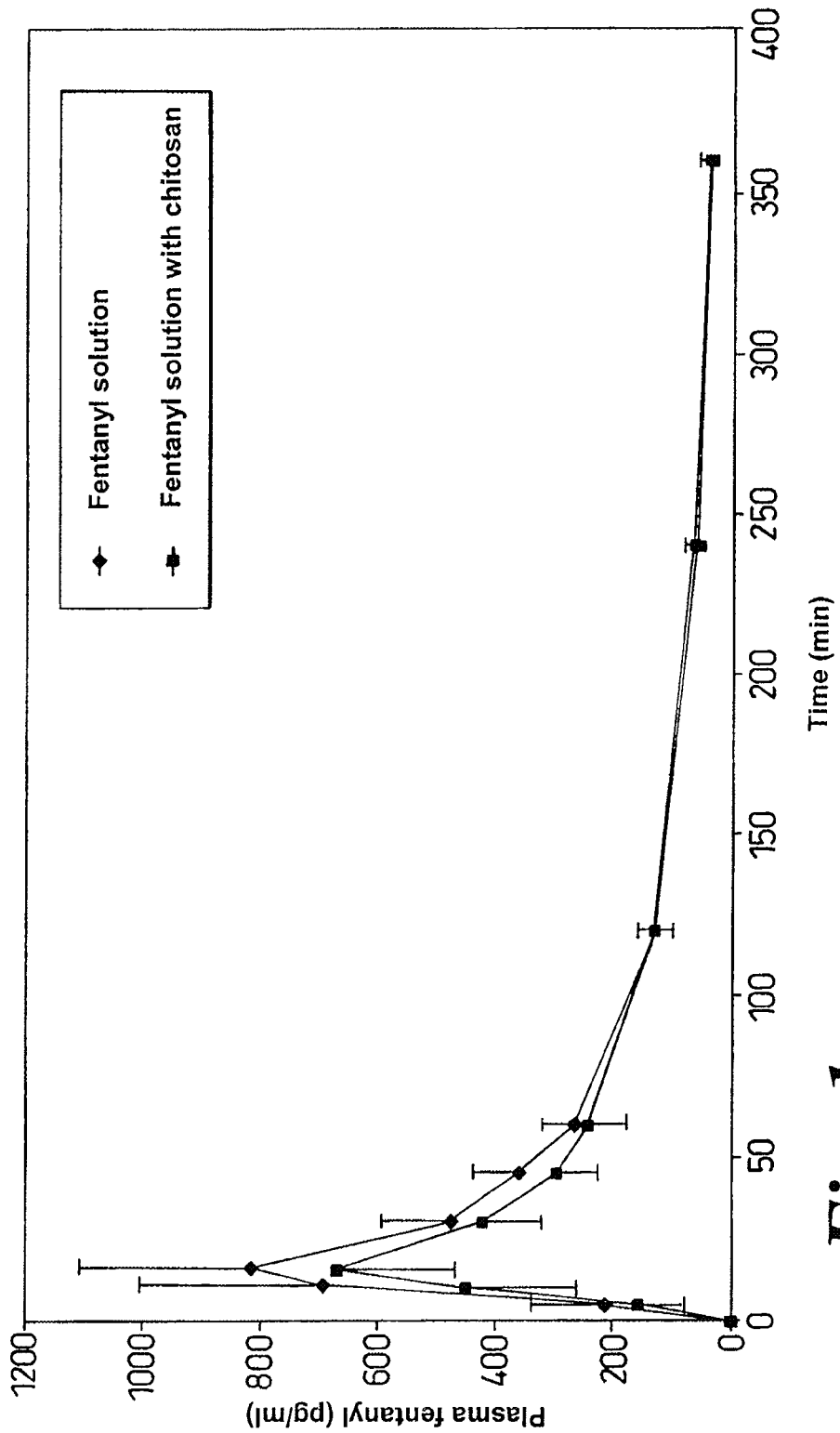
FIG. 1 shows mean plasma concentration profiles of fentanyl following the administration of a fentanyl solution comprising chitosan and a fentanyl solution that did not contain chitosan to sheep obtained in Example 7.

Surprisingly, it has been found that it is possible to administer fentanyl intranasally in a practical dose volume and provide rapid absorption in combination with a lower peak plasma concentration than that provided using a simple aqueous solution and an extended plasma concentration-time profile. These advantages can be achieved while maintaining a bioavailability that is comparable to that obtained by the intranasal administration of a simple aqueous solution comprising fentanyl.

By "comparable bioavailability," it is meant that the area under the plasma concentration vs. time curve (AUC) is at least 50%, more preferably at least 60% and most preferably at least 70% of that for a simple aqueous solution of fentanyl administered intranasally at the same dose.

By "simple aqueous solution," it is meant fentanyl and an ingredient to make the solution isotonic, such as mannitol, dextrose or sodium chloride, dissolved in water. A simple aqueous solution may optionally contain a preservative, such as benzalkonium chloride. An example of such a simple aqueous solution comprises 1.57 mg/ml fentanyl citrate, 48 mg/ml mannitol and 0.15 mg/ml benzalkonium chloride in water.

The present invention provides a composition for the intranasal delivery of fentanyl or a pharmaceutically acceptable salt thereof to an animal, which comprises an aqueous solution of
- fentanyl or a pharmaceutically acceptable salt thereof and
- a pharmaceutically acceptable additive selected from
- a pectin and
- a poloxamer and chitosan or a salt or derivative thereof;
- provided that when the composition comprises a pectin it is substantially free of agents that cause the pectin to gel, such as divalent metal ions, especially calcium ions.

The additive may be a pectin, a poloxamer, a chitosan (or a salt or derivative thereof) or it may be a mix of two or more of these additives.

In comparison to a simple aqueous solution of fentanyl administered intranasally at the same dose, the compositions of the present invention provide a lowered peak plasma concentration of fentanyl ($C_{max}$) and optionally an extended plasma-concentration time profile. The peak plasma concentration ($C_{max}$) achieved using a composition of the present invention is from 10 to 80%, preferably from 20 to 75% and more preferably from 30 to 70% of that achieved using a simple aqueous solution administered intranasally at an identical fentanyl dose. This means, for example, if a simple aqueous solution of fentanyl produces a $C_{max}$ of 1000 µg/ml, the $C_{max}$ produced by a composition of this invention following administration of an identical dose of fentanyl, is in the range 100-800 µg/ml, preferably 200-750 µg/ml and more preferably 300-700 µg/ml.

The time to achieve the peak plasma concentration ($T_{max}$) by nasal administration of a composition of the present invention is preferably from 5 to 60 minutes, more preferably from 5 to 45 minutes and most preferably from 5 to 30 minutes.

Fentanyl is preferably used in the form of a pharmaceutically acceptable salt. Most preferably fentanyl citrate is used.

The concentration of fentanyl or a salt thereof in the compositions of the invention is preferably in the range of from 0.05 to 30 mg/ml, more preferably from 0.1 to 20 mg/ml and most preferably from 0.2 to 16 mg/ml (expressed as fentanyl base).

The term "pharmaceutically acceptable" is readily understood in the art and can be considered to include materials that may be used in commercially available pharmaceutical or food products and/or have GRAS (generally regarded as safe) status and/or are listed in a pharmacopoeia such as the United States Pharmacopoeia or the European Pharmacopoeia.

In one aspect, the present invention provides a composition for the intranasal delivery of fentanyl or a pharmaceutically acceptable salt thereof, comprising an aqueous solution of fentanyl or a pharmaceutically acceptable salt thereof and a pectin and which provides a peak plasma concentration ($C_{max}$) of fentanyl of from 10 to 80% of that achieved using a simple aqueous solution administered intranasally at an identical fentanyl dose.

Pectins are polysaccharide substances present in the cell walls of all plant tissues. Commercially they are generally obtained from the dilute acid extract of the inner portion of the rind of citrus fruits or from apple pomace. Pectins are heterogeneous materials, comprising partially methoxylated polygalacturonic acids.

The proportion of galacturonic acid moieties in the methyl ester form represents the degree of esterification (DE). The term "DE" is well understood by those skilled in the art and may be represented as the percentage of the total number of carboxyl groups that are esterified, i.e., if four out of five acid groups is esterified this represents a degree of esterification of 80%, or as the methoxyl content of the pectin. The respective theoretical maximum for each is 100% and 16% respectively. "DE" as used herein refers to the total percentage of carboxyl groups that are esterified. The degree of esterification (DE) of pectins found naturally can vary considerably (from 60 to 90%).

Pectins can be categorized into those having a low degree of esterification (low methoxylation) or a high degree of esterification (high methoxylation). A "low DE" or "LM" pectin has a degree of esterification below 50% whereas a "high DE" or "HM" pectin has a degree of esterification of 50% or above.

The gelling properties of aqueous pectin solutions can be controlled by the concentration of pectin, the type of pectin, especially the degree of esterification of the galacturonic acid units, and the presence of added salts.

Preferably low DE pectins are used in the compositions of the present invention. More preferably pectins having a degree of esterification of less than 35%, for example from 5 to 35%, preferably from 7 to 30%, such as from about 10 to about 25%, for example from 15 to 25% are used in the present invention.

Low DE pectins are usually prepared by the de-esterification of extracted pectins, normally on a bench scale, by way of an enzymatic process, or, on an industrial scale, by treatment with acid or ammonia in an alcoholic heterogeneous medium. Treatment with ammonia creates so-called low DE amidated pectins. As used herein, the term "low DE pectin" includes both amidated and non-amidated low DE pectins.

Low DE pectins may be purchased commercially. An example of a low DE pectin which may be used in the present invention is SLENDID® 100, supplied by CP Kelco (Lille Skensved, Denmark) which has a degree of esterification of about 15 to 25%.

The primary mechanism by which low DE pectins gel in aqueous solution is through exposure to metal ions, such as those found in the nasal mucosal fluid as described in WO98/47535.

The solutions of the invention should not gel on storage. Thus, solutions containing a pectin are substantially free of agents that cause the pectin to gel, such as divalent metal ions, especially calcium ions. By "substantially free" of divalent metal ions it is meant greater than 97%, preferably greater than 99%, more preferably greater than 99.9% and especially greater than 99.99% free of divalent metal ions.

When a composition of the invention contains a pectin, the concentration of pectin is preferably in the range of from 1 to 40 mg/ml, more preferably from 2 to 30 mg/ml and most preferably from 5 to 25 mg/ml.

A preferred pectin containing composition of the invention comprises 0.2 to 16 mg/ml of fentanyl (expressed as fentanyl base) and 5 to 25 mg/ml of a pectin having a DE value of from 7 to 30% and has a pH of from 3.4 to 5.0 and an osmolality of from 0.25 to 0.35 osmol/kg.

In one aspect, the present invention provides a composition comprising fentanyl or a pharmaceutically acceptable salt thereof and a poloxamer and chitosan or a salt or derivative thereof.

Poloxamers are block copolymers of ethylene oxide and propylene oxide. They have the general formula $HO(C_2H_4O)_a(C_3H_6O)_b(C_2H_4O)_aH$ wherein a is typically from 2 to 130 and b is typically from 15 to 67. Poloxamers have a number of pharmaceutical applications such as viscosity modifiers, solubilising agents or emulsifiers. They may be used in the compositions of the present invention as thickening agents and in order to control and modify the absorption of fentanyl into the systemic circulation such that a peak plasma concentration ($C_{max}$) of fentanyl of from 10 to 80% of that achieved using a simple aqueous solution administered intranasally at an identical fentanyl dose is achieved.

Several different types of poloxamer are available commercially, from suppliers such as BASF, and vary with respect to molecular weight and the proportions of ethylene oxide "a" units and propylene oxide "b" units. Poloxamers suitable for use in the present invention typically have a molecular weight of from 2,500 to 18,000, for example from 7,000 to 15,000 Da. Examples of commercially available poloxamers suitable for use in the present invention include poloxamer 188, which structurally contains 80 "a" units and 27 "b" units, and has a molecular weight in the range 7680 to 9510 and poloxamer 407 which structurally contains 101 "a" units and 56 "b" units, and has a molecular weight in the range 9840 to 14600 (Handbook of Pharmaceutical Excipients, editor A. H. Kippe, $3^{rd}$ edition, Pharmaceutical Press, London, United Kingdom, 2000). Preferably the poloxamer is poloxamer 188.

When the compositions of the present invention comprise a poloxamer, the poloxamer is preferably present at a concentration in the range of from 50 to 200 mg/ml, more preferably from 65 to 160 mg/ml and most preferably from 80 to 120 mg/ml.

Compositions of the invention that comprise a poloxamer also comprise chitosan or a salt or derivative thereof.

Chitosans are cationic polymers that have mucoadhesive properties. The mucoadhesion is thought to result from an interaction between the positively charged chitosan molecule and the negatively charged sialic acid groups on mucin (Soane et al. Int. J. Pharm., 178, 55-65, 1999).

By the term "chitosan," it is meant all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation). Preferably, the chitosan is produced from chitin by deacetylation to a degree of greater than 40%, preferably between 50 and 98%, more preferably between 70% and 90%.

The chitosan, chitosan derivative, or salt used in the present invention preferably has a molecular weight of 4,000 Da or more, preferably from 10,000 to 1,000,000 Da, more preferably from 15,000 to 750,000 Da and most preferably from 50,000 to 300,000 Da.

Salts of chitosan are suitable for use in the present invention. Suitable salts include, but are not limited to, the nitrate, phosphate, glutamate, lactate, citrate, hydrochloride and acetate salts. Preferred salts are chitosan glutamate and chitosan hydrochloride.

Chitosan derivatives are also suitable for use in the present invention. Suitable chitosan derivatives include, but are not limited to, ester, ether or other derivatives formed by bonding acyl and/or alkyl groups with the hydroxyl groups, but not the amino groups of chitosan. Examples are O-alkyl ethers of chitosan and O-acyl esters of chitosan. Modified chitosans, such as those conjugated to polyethylene glycol may be used in the present invention.

Low and medium viscosity chitosans suitable for use in the present invention may be obtained from various sources, including NovaMatrix, Drammen, Norway; Seigagaku America Inc., Maryland, United States of America; Meron (India) Pvt, Ltd., India; Vanson Ltd, Virginia, United States of America; and AMS Biotechnology Ltd., United Kingdom. Suitable derivatives include those that are disclosed in Roberts, Chitin Chemistry, MacMillan Press Ltd., London (1992).

Particularly preferred chitosan compounds that may be mentioned include the "PROTOSAN™" types available from NovaMatrix, Drammen, Norway.

Preferably, the chitosan, or salt or derivative thereof is water-soluble.

An aqueous solution of chitosan may be prepared by dissolving chitosan base or a derivative of chitosan base in a pharmaceutically acceptable mineral or organic acid such as hydrochloric, lactic, citric or glutamic acid or by dissolving a chitosan salt or a salt of a chitosan derivative in water.

When the compositions of the present invention comprise chitosan, a chitosan salt or a chitosan derivative, the concentration of chitosan is preferably from 0.1 to 20 mg/ml, more preferably from 0.5 to 15 mg/ml and most preferably from 1 to 10 mg/ml (expressed as chitosan base).

A preferred poloxamer and chitosan containing composition of the invention comprises 0.2 to 16 mg/ml of fentanyl (expressed as fentanyl base), 80 to 120 mg/ml of a poloxamer having a molecular weight of from 7,000 to 15,000 Da and 1 to 10 mg/ml (expressed as chitosan base) of a chitosan having a molecular weight of from 50,000 to 300,000 Da or a salt or derivative thereof and has a pH of from 3.0 to 5.0 and an osmolality of from 0.4 to 0.7 osmol/kg.

The pH of the compositions of the invention may be regulated. For example, buffered aqueous solutions may be used. Alternatively, the pH of the compositions of the present invention may be adjusted using any pharmaceutically acceptable acidifying or alkalizing agent that is compatible with the other components of the compositions. Examples of suitable pharmaceutically acceptable acidifying agents include, but are not limited to, hydrochloric acid, acetic acid, citric acid, methane sulphonic acid, lactic acid, tartaric acid, fumaric acid and malic acid. Examples of pharmaceutically acceptable alkalizing agents include, but are not limited to, sodium hydroxide, potassium hydroxide, meglumine, tromethamine, sodium bicarbonate, monoethanolamine, diethanolamine and triethanolamine. When the composition of the invention contains pectin, in order to prevent unwanted gelling, the acidifying agent or alkalizing agent preferably should not contain an alkali metal or alkaline earth metal ion, for example it should not be sodium hydroxide, potassium hydroxide or sodium bicarbonate.

The pH of the compositions of the invention is generally preferably from 3 to 6. For the pectin containing compositions of the invention, the pH is more preferably from 3.2 to 5.5 and most preferably from 3.4 to 5.0. For the poloxamer- and chitosan-containing compositions of the invention, the pH is more preferably from 3.0 to 5.5 and most preferably from 3.0 to 5.0.

To ensure that the compositions of the invention are well tolerated by the patient when administered to the nose (for example when sprayed into the nasal cavity), it is advantageous that they have an osmolality close to that of plasma. The osmolality is generally preferably from 0.1 to 1.0 osmol/kg. For the pectin-containing compositions of the invention, the osmolality is more preferably from 0.2 to 0.8 osmol/kg, still more preferably from 0.2 to 0.4 osmol/kg and most preferably from 0.25 to 0.35 osmol/kg. For the poloxamer- and chitosan-containing compositions of the invention, the osmolality is more preferably from 0.2 to 0.9 osmol/kg, still more preferably from 0.3 to 0.8 osmol/kg and most preferably from 0.4 to 0.7 osmol/kg.

The osmolality of the compositions of the invention may be adjusted to the desired value by adding any appropriate agent. Salts of metal ions, in particular sodium chloride, are commonly used to adjust the osmolality of pharmaceutical preparations. However, it is not appropriate to use metal ions when the composition of the invention includes a pectin because pectins may form a gel in the presence of metal ions. It has been found that addition of metal ions, for example sodium in the form of sodium chloride, to compositions containing fentanyl and chitosan results in the formation of a precipitate. Thus, the use of metal ion containing agents should preferably be avoided. We have found that gel formation in pectin-containing fentanyl compositions and precipitate formation in chitosan-containing fentanyl compositions can be avoided by using a non-metal ion-containing compound such as a polyhydric alcohol, for example mannitol or sorbitol, or a sugar, for example dextrose, sucrose or trehalose, to adjust the osmolality. Especially preferred agents to adjust osmolality are mannitol and dextrose at a concentration of up to 50 mg/ml.

The compositions of the invention may also contain other ingredients such as antioxidants (for example sodium metabisulphite), chelating agents (such as edetic acid or one of its salts), preservatives (such as benzalkonium chloride, sorbic acid or one of its salts, phenylethyl alcohol and/or propyl hydroxybenzoate), sweeteners (such as saccharin or aspartame), flavorings (such as peppermint) or other agents generally used in pharmaceutical liquid preparations and well known to those skilled in the art.

Preferably, the compositions of the invention contain a preservative or are sterile.

Preferably, the compositions of the invention are non-pyrogenic.

The composition of the invention can be administered to the nasal cavity in any suitable form, for example in the form of drops or sprays.

Methods suitable for administering a composition to the nasal cavity will be well known by the person of ordinary skill in the art. Any suitable method may be used. The preferred method of administration is the use of a spray device. Spray devices can be single (unit) dose or multiple dose systems, for example comprising a bottle, pump and actuator, and are available from various commercial sources including Pfeiffer, Valois, Bespak and Becton-Dickinson. Electrostatic spray devices, such as described in U.S. Pat. No. 5,655,517, are also suitable for the intranasal administration of the compositions of the present invention.

For a spray device, the typical volume of liquid that is dispensed in a single spray actuation is in the range of from 0.01 to 0.15 ml. A typical dosing regimen for a nasal spray product would be in the range of one spray into a single nostril to two sprays into each nostril.

The preferred dose of fentanyl or one of its salts is from 0.01 to 5.0 mg (10 to 5000 µg), more preferably from 0.015 to 4.0 mg (15 to 4000 µg) and most preferably from 0.02 to 3.0 mg (20 to 3000 µg).

The present invention also provides a spray device loaded with a composition as defined above.

The present invention also provides a process for preparing a composition as described above. This process comprises mixing the components of the composition in water. Purified water such as water for injections may be used.

The compositions of this invention can be used for the treatment, management or prevention of both acute and chronic pain, in animals including humans. The compositions of the invention can be used to treat, manage or prevent pain a wide variety of pain conditions such as those associated with injury and accident trauma, terminal illness, especially breakthrough pain, and following surgery.

The present invention also provides the use of a pharmaceutically acceptable additive selected from
(a) a pectin and
(b) a poloxamer and chitosan or a salt or derivative thereof;
in the manufacture of a medicament for the intranasal delivery of fentanyl or a pharmaceutically acceptable salt thereof to an animal such as a human in need thereof, which medicament is adapted to provide a peak plasma concentration of fentanyl ($C_{max}$) that is from 10 to 80% of that achieved using a simple aqueous solution of fentanyl administered intranasally at an identical fentanyl dose.

In particular, the present invention provides the use of a pharmaceutically acceptable additive selected from
(a) a pectin and
(b) a poloxamer and chitosan or a salt or derivative thereof;
in the manufacture of a medicament for the intranasal delivery of fentanyl or a pharmaceutically acceptable salt thereof to an animal such as a human in need thereof suitable for the treatment, prevention or management of acute or chronic pain, which medicament is adapted to provide a peak plasma concentration of fentanyl ($C_{max}$) that is from 10 to 80% of that achieved using a simple aqueous solution of fentanyl administered intranasally at an identical fentanyl dose.

The invention is illustrated by the following non-limiting examples.

EXAMPLES

Example 1

Solution Containing 1.57 mg/ml Fentanyl Citrate (Equivalent to 1 mg/ml Fentanyl Base) and 10 mg/ml Pectin 2 g of pectin (SLENDID™ 100, CP Kelco, Denmark) was dissolved with stirring in 180 ml of water. 1 ml of phenylethyl alcohol (R. C. Treat, United Kingdom) and 40 mg of propyl hydroxybenzoate (Nipa Laboratories, United Kingdom) were added to the pectin solution as preservatives. 314 mg of fentanyl citrate (MacFarlan Smith, Edinburgh, United Kingdom) and 8.3 g of mannitol (Sigma, Poole, United Kingdom) were dissolved in the pectin solution, the solution transferred to a 200 ml volumetric flask and made up to volume with water. The pH of the solution was 4.2 and the osmolality was 0.33 osmol/kg.

Example 2

Solution Containing 1.57 mg/ml Fentanyl Citrate and 20 mg/ml Pectin 4 g of pectin (SLENDID 100) was dissolved with stirring in 180 ml of water. 1 ml of phenylethyl alcohol and 40 mg of propyl hydroxybenzoate were added to the pectin solution. 314 mg of fentanyl citrate and 8.3 g of mannitol were dissolved in the pectin solution, the solution was transferred to a 200 ml volumetric flask and made up to volume with water.

4 ml of the solution was transferred into a 5 ml glass bottle. A Valois VP7 spray pump (0.1 ml volume) with actuator (Valois, France) was attached to bottle. The pump was primed by firing several times. When primed, firing the device delivered 0.1 ml of liquid spray containing 0.157 mg of fentanyl citrate (equivalent to 0.1 mg of fentanyl base).

Example 3

Solution Containing 1.57 mg/ml Fentanyl Citrate, 100 mg/ml Poloxamer 188 and 5 mg/ml Chitosan Glutamate A 15 mg/ml benzalkonium chloride solution was prepared by weighing 300 mg of 50% benzalkonium chloride aqueous solution (Albright & Wilson, United Kingdom) into a 10 ml volumetric flask, dispersing it in approximately 8 ml of water, then making the solution up to 10 ml with water.

2.5 ml of 15 mg/ml benzalkonium chloride solution and 200 ml of water were added to 25 g of poloxamer 188 in a beaker. The beaker was placed in an ice bath and the contents stirred until the poloxamer had dissolved. 1.25 g of chitosan glutamate (PROTASAN™ UPG213, Pronova, Norway) and 11.25 g of mannitol were stirred into the poloxamer solution until dissolved. 393 mg of fentanyl citrate was dissolved in approximately 10 ml of water and added to the poloxamer solution. The solution was transferred into a 250 ml volumetric flask and made up to volume with water.

The pH of the solution was 3.3 and the osmolality was 0.56 osmol/kg.

0.123 ml samples of the final solution were filled into the glass vial of a single dose nasal spray device (Unitdose System, Pfeiffer, Germany). The vial was sealed with a rubber closure and assembled into the device. On firing, the device emitted 0.1 ml of liquid spray containing a 0.157 mg dose of fentanyl citrate (equivalent to 0.1 mg fentanyl base).

Example 4

Solution Containing 6.28 mg/ml Fentanyl Citrate (Equivalent to 4 mg/ml Fentanyl Base) and 10 mg/ml Pectin 2.5 g of pectin (SLENDID™ 100) was dissolved with stirring in 200 ml of water. 1.25 ml of phenylethyl alcohol and 50 mg of propyl hydroxybenzoate were added to the pectin solution. 1.58 mg of fentanyl citrate and 9 g of mannitol were dissolved in the pectin solution, the solution transferred to a 250 ml volumetric flask and made up to volume with water.

The pH of the solution was 3.8 and the osmolality was 0.30 osmol/kg.

0.123 ml samples of the final solution were filled into the glass vial of a single dose nasal spray device (Unitdose System, Pfeiffer, Germany). The vial was sealed with a rubber closure and assembled into the device. On firing, the device emitted 0.1 ml of liquid spray containing a 0.628 mg dose of fentanyl citrate (equivalent to 0.4 mg fentanyl base).

Example 5

Preparation of Solution Containing 1.57 mg/ml Fentanyl Citrate 78.5 mg of fentanyl citrate was dissolved in 40 ml of water. 0.5 ml of 15 mg/ml benzalkonium chloride solution and 2.4 g mannitol were added to the fentanyl solution which was stirred until all of the ingredients had dissolved. The solution was transferred to a 50 ml volumetric flask and made up to volume with water.

Example 6

Preparation of Solution Containing 1.57 mg/ml Fentanyl Citrate and 5 mg/ml Chitosan Glutamate 250 mg of chitosan glutamate was dissolved in 40 ml of water. 0.5 ml of 15 mg/ml benzalkonium chloride solution, 78.5 mg fentanyl citrate and 2.4 g mannitol were added to the chitosan solution which was stirred until all of the ingredients had dissolved. The solution was transferred to a 50 ml volumetric flask and made up to volume with water.

Example 7

Pharmacokinetic Performance of Fentanyl Intranasal Formulations in the Sheep

The solutions prepared in Examples 5 and 6 were administered intranasally to sheep. A group of eight animals, each weighing approximately 60 kg, was used. The doses were administered to a randomized crossover design and each animal received 0.3 ml of each test solution (equivalent to 0.3 mg fentanyl base) intranasally. Nasal doses were administered via a spray device with the dose volume being divided equally between both nostrils.

Blood samples were collected and plasma separated. Plasma samples were assayed by a LC-MS-MS method for fentanyl content.

Mean plasma concentration-time curves for the two nasal test solutions are shown in FIG. 1. The curves were essentially identical and indicated that fentanyl was rapidly absorbed both in the absence and presence of chitosan.

Example 8

Pharmacokinetic Performance of Fentanyl Intranasal and Oral Transmucosal Formulations in Human Volunteers A clinical study was performed to evaluate the pharmacokinetic performance of three intranasal fentanyl formulations and a transmucosal lozenge formulation (ACTIQ®, Elan Pharmaceuticals, United Kingdom).

The intranasal formulations were prepared as described Examples 1, 3, and 6 above.

The study was a randomized four-way complete cross-over trial in a group of 18 healthy adult volunteers. Intranasal doses were administered using Pfeiffer Unitdose devices. Each subject received a single spray into one nostril to provide a fentanyl dose of 0.1 mg. The ACTIQ® dose was provided as a lozenge containing 200 µg (0.2 mg) of fentanyl. The lozenge was administered by dissolving in the mouth over a period of approximately 15 minutes. Plasma samples were collected from the subjects and analyzed for fentanyl content using a LC-MS-MS assay. Pharmacokinetic parameters were calculated from the plasma data.

Figure 2:
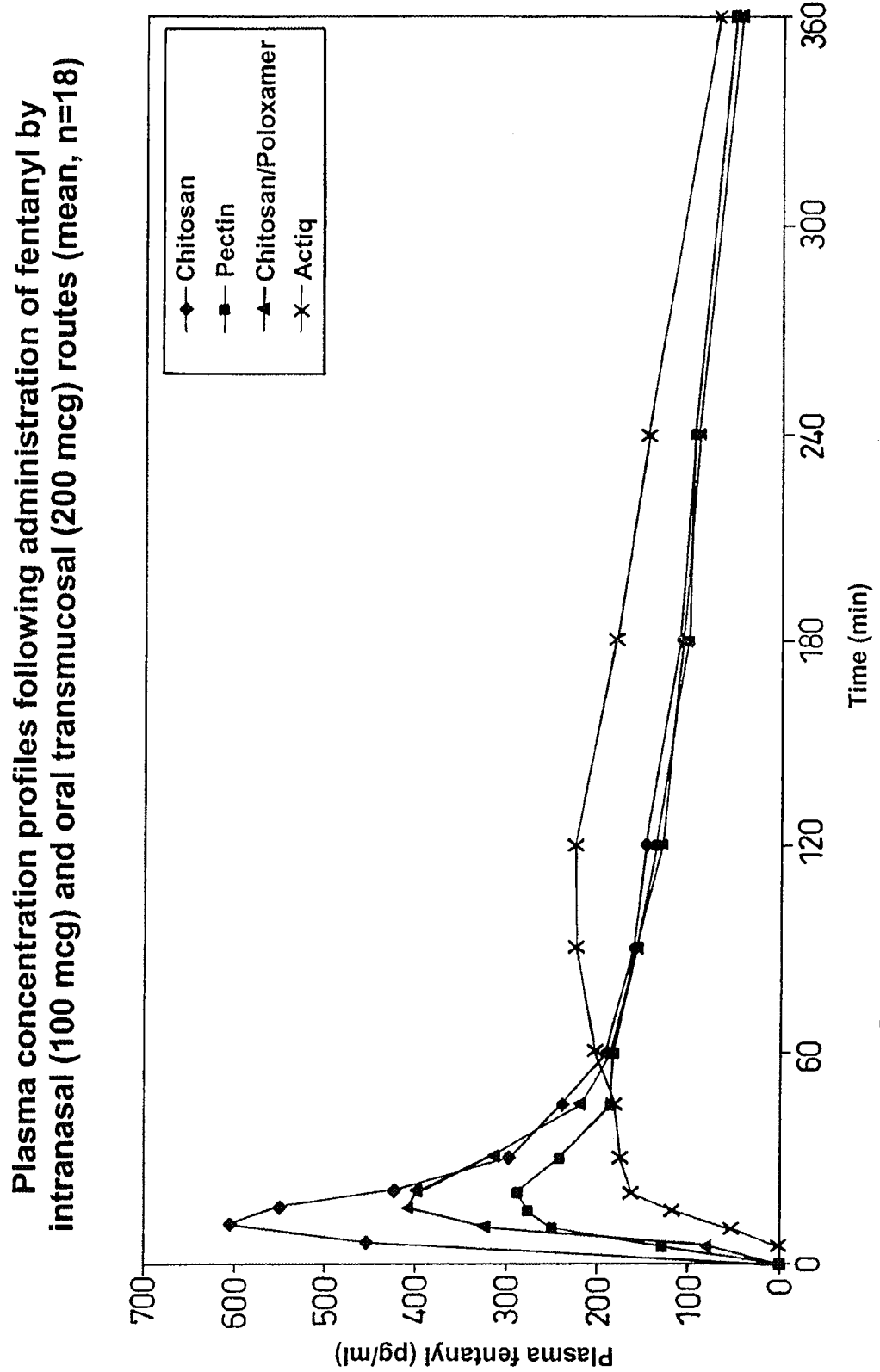
FIG. 2 shows plasma concentration of fentanyl profiles for three intranasal and one transmucosal formulation obtained in Example 8.

Plasma concentration versus time curves for the three intranasal and one transmucosal formulation are shown in FIG. 2. A summary of the pharmacokinetic parameters is provided in Table 1.

TABLE 1

Summary of mean fentanyl pharmacokinetic parameters.

| Formulation | $T_{max}$ (min) | $C_{max}$ (pg/ml) | AUC (pg/ml · h) | Bioavailability relative to ACTIQ ® (%) |
|---|---|---|---|---|
| Nasal chitosan solution | 12 | 647 | 95747 | 166 |
| Nasal pectin solution | 21 | 337 | 87079 | 147 |
| Nasal poloxamer + chitosan solution | 18 | 442 | 82614 | 143 |
| ACTIQ ® (oral transmucosal) | 101 | 264 | 117840 | (100) |

Based on the results from the sheep study described in Example 7, the pharmacokinetic performance of the chitosan solution in the human volunteer study can be considered to be representative of a simple aqueous solution of fentanyl. The intranasal formulations containing pectin and a mixture of poloxamer and chitosan were able to reduce the $C_{max}$ to values of 52% and 68% respectively relative to the nasal chitosan solution.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating or managing pain comprising intranasally administering to an animal in need thereof in a single dosage regimen in an amount to effectively treat or manage pain, a pharmaceutical composition comprising an aqueous solution of
    fentanyl or a pharmaceutically acceptable salt thereof in an amount to effectively treat or manage pain and
    a pectin having a degree of esterification (DE value) of less than 30%, provided that the composition is substantially free of divalent metal ions;
    wherein the animal administered the composition is provided with a peak plasma concentration of fentanyl ($C_{max}$) that is from 10 to 80% of that achieved using a simple aqueous solution of fentanyl administered intranasally at an identical fentanyl dose; and
    wherein the intranasal administration of the composition provides a time to achieve peak plasma concentration ($T_{max}$) of fentanyl in the animal's plasma of 5 to 30 minutes.

2. A method according to claim 1, wherein the animal administered the composition is provided with a peak plasma concentration of fentanyl ($C_{max}$) that is from 20 to 75% of that achieved using a simple aqueous solution of fentanyl administered intranasally at an identical fentanyl dose.

3. A method according to claim 2, wherein the animal administered the composition is provided with a peak plasma concentration of fentanyl ($C_{max}$) that is from 30 to 70% of that achieved using a simple aqueous solution of fentanyl administered intranasally at an identical fentanyl dose.

4. A method according to claim 1, wherein the pectin has a DE value of from 7 to 30%.

5. A method according to claim 4, wherein the pectin has a DE value of from 10 to 25%.

6. A method according to claim 5, wherein the pectin has a DE value of from 15 to 25%.

7. A method according to claim 1, wherein the animal administered the composition is provided with a peak plasma concentration of fentanyl ($C_{max}$) that is from 20 to 75% of that achieved using a simple aqueous solution of fentanyl administered intranasally at an identical fentanyl dose, and wherein the pectin has a DE value of from 7 to 30%.

8. A method according to claim 6, wherein the animal administered the composition is provided with a peak plasma concentration of fentanyl ($C_{max}$) that is from 20 to 75% of that achieved using a simple aqueous solution of fentanyl administered intranasally at an identical fentanyl dose, and wherein the pectin has a DE value of from 10 to 25%.

9. A method according to claim 8, wherein the animal administered the composition is provided with a peak plasma concentration of fentanyl ($C_{max}$) that is from 30 to 70% of that achieved using a simple aqueous solution of fentanyl administered intranasally at an identical fentanyl dose, and wherein the pectin has a DE value of from 15 to 25%.

10. A method according to claim 1, wherein the composition comprises a pharmaceutically acceptable salt of fentanyl.

11. A method according to claim 10, wherein the pharmaceutically acceptable salt of fentanyl is fentanyl citrate.

12. A method according to claim 1, wherein the composition has a concentration of pectin from 5 to 25 mg/ml of the composition.

13. A method according to claim 1, wherein the composition is at least 99% free of divalent metal ions.

14. A method according to claim 1, wherein the composition has an osmolality of from 0.2 to 0.8 osmol/kg.

15. A method according to claim 14, wherein the composition has an osmolality of from 0.2 to 0.4 osmol/kg.

16. A method according to claim 1, wherein the composition has a pH of from 3 to 6.

17. A method according to claim 16, wherein the composition has a pH of from 3.2 to 5.5.

18. A method according to claim 17, wherein the composition has a pH of from 3.4 to 5.0.

19. A method according to claim 1, wherein the composition is administered in the form of drops or as a spray.

20. A method according to claim 1 for treating acute or chronic pain.

21. A method according to claim 1, wherein the animal is a human.

22. A method according to claim 21, wherein the method further comprises administering the composition to the human via a maximum of two intranasal sprays to each nostril of the human where the maximum volume of each spray is 0.15 ml of the composition.

23. A method according to claim 1, wherein the composition comprises from 0.05 to 30 mg/ml of the composition of fentanyl or a pharmaceutically acceptable salt thereof (expressed as fentanyl base).

24. A method according to claim 23, wherein the composition comprises from 0.1 to 20 mg/ml of fentanyl or a pharmaceutically acceptable salt thereof (expressed as fentanyl base).

25. A method according to claim 24, wherein the composition comprises from 0.2 to 16 mg/ml of fentanyl or a pharmaceutically acceptable salt thereof (expressed as fentanyl base) of the composition.

26. A method according to claim 1, in which fentanyl or a pharmaceutically acceptable salt thereof (expressed as fentanyl base) is delivered at a dose of from 10 to 3000 µg.

27. A method of treating or managing pain comprising intranasally administering to an animal in need thereof in a single dosage regimen in an amount to effectively treat or manage pain, a pharmaceutical composition comprising an aqueous solution of
    0.05 to 16 mg/ml (expressed as fentanyl base) of fentanyl or a pharmaceutically acceptable salt thereof and 5 to 25 mg/ml of a pectin having a DE value of 10 to 25%;
the composition having a pH of 3.4 to 5.0 and an osmolality of 0.2 to 0.4 osmol/kg and being substantially free of divalent metal ions;
so as to provide in the animal administered the composition a peak plasma concentration of fentanyl ($C_{max}$) that is from 20 to 75% of that achieved using a simple aqueous solution of fentanyl administered intranasally at an identical fentanyl dose and a time to achieve peak plasma concentration ($T_{max}$) of fentanyl in the animal's plasma of 5 to 30 minutes.

28. A method according to claim 27, wherein the composition comprises from 0.2 to 16 mg/ml (expressed as fentanyl base) of fentanyl or a pharmaceutically acceptable salt thereof.

29. A method according to claim 27, wherein the animal is a human.

30. A method according to claim 29, wherein the method further comprises administering the composition to the human via a maximum of two intranasal sprays to each nostril of the human where the maximum volume of each spray is 0.15 ml of the composition.

31. A method of treating or managing pain comprising intranasally administering to an animal in need thereof in a single dosage regimen in an amount to effectively treat or manage pain, a pharmaceutical composition comprising an aqueous solution of
fentanyl or a pharmaceutically acceptable salt thereof in an amount to effectively treat or manage pain that is from 0.05 to 30 mg/ml of fentanyl or a pharmaceutically acceptable salt thereof (expressed as fentanyl base);
a pectin having a degree of esterification (DE value) of less than 30%; and
a non-metal ion osmolality adjusting agent in an amount to ensure that the osmolality of the composition is from 0.2 to 0.8 osmol/kg;
provided that the composition is substantially free of divalent metal ions;
wherein the animal administered the composition is provided with a peak plasma concentration of fentanyl ($C_{max}$) that is from 20 to 75% of that achieved using a simple aqueous solution of fentanyl administered intranasally at an identical fentanyl dose; and
wherein the intranasal administration of the composition provides a time to achieve peak plasma concentration ($T_{max}$) of fentanyl in the animal's plasma of 5 to 30 minutes.

32. The method of claim 31, wherein the non-metal ion osmolality adjusting agent is selected from one or more in the group consisting of mannitol, sorbitol, dextrose, sucrose and trehalose.

33. The method of claim 31, wherein the osmolality of the composition is from 0.2 to 0.4 osmol/kg.

34. A method according to claim 31, wherein the composition comprises from 0.1 to 20 mg/ml of fentanyl or a pharmaceutically acceptable salt thereof (expressed as fentanyl base).

35. A method according to claim 34, wherein the composition comprises from 0.2 to 16 mg/ml of fentanyl or a pharmaceutically acceptable salt thereof (expressed as fentanyl base).

36. A method according to claim 31, in which fentanyl or a pharmaceutically acceptable salt thereof (expressed as fentanyl base) is delivered at a dose of from 10 to 3000 µg.

37. The method of claim 33, wherein the osmolality of the composition is from 0.25 to 0.35 osmol/kg.

38. A method according to claim 31, wherein the composition has a pH of from 3 to 6.

39. A method according to claim 38, wherein the composition has a pH of from 3.2 to 5.5.

40. A method according to claim 39, wherein the composition has a pH of from 3.4 to 5.0.

* * * * *